(12) United States Patent
 Soliman

(10) Patent No.: US 10,874,295 B2
(45) Date of Patent: Dec. 29, 2020

(54) MEDICAL IMAGING SYSTEM AND DEVICE

(71) Applicant: Alaaeldin Soliman, Holmdel, NJ (US)

(72) Inventor: Alaaeldin Soliman, Holmdel, NJ (US)

( * ) Notice: Subject to any disclaimer, the term of this patent is extended or adjusted under 35 U.S.C. 154(b) by 1031 days.

(21) Appl. No.: 15/369,883

(22) Filed: Dec. 5, 2016

(65) Prior Publication Data

US 2018/0153388 A1 Jun. 7, 2018

(51) Int. Cl.

| | |
|---|---|
| *A61B 1/00* | (2006.01) |
| *A61B 1/267* | (2006.01) |
| *A61B 1/05* | (2006.01) |
| *A61B 1/012* | (2006.01) |
| *A61B 5/042* | (2006.01) |
| *A61B 5/03* | (2006.01) |
| *A61B 1/273* | (2006.01) |
| *A61M 16/04* | (2006.01) |
| *A61J 15/00* | (2006.01) |
| *A61B 7/04* | (2006.01) |
| *A61B 5/00* | (2006.01) |

(52) U.S. Cl.
CPC .............. *A61B 1/267* (2013.01); *A61B 1/012* (2013.01); *A61B 1/05* (2013.01); *A61B 1/2736* (2013.01); *A61B 5/037* (2013.01); *A61B 5/0421* (2013.01); *A61J 15/0003* (2013.01); *A61J 15/0073* (2013.01); *A61J 15/0084* (2015.05); *A61J 15/0088* (2015.05); *A61M 16/0411* (2014.02); *A61M 16/0415* (2014.02); *A61M 16/0488* (2013.01); *A61B 5/6853* (2013.01); *A61B 7/04* (2013.01); *A61J 15/0049* (2013.01); *A61M 2205/32* (2013.01); *A61M 2205/332* (2013.01); *A61M 2205/3344* (2013.01); *A61M 2205/3375* (2013.01); *A61M 2205/502* (2013.01); *A61M 2210/105* (2013.01); *A61M 2230/04* (2013.01)

(58) Field of Classification Search
CPC ..... A61B 1/267; A61B 1/2736; A61B 1/0125; A61B 1/00177; A61M 16/04
See application file for complete search history.

(56) References Cited

U.S. PATENT DOCUMENTS

2003/0018276 A1\* 1/2003 Mansy .................. A61B 7/003
 600/529
2008/0051629 A1\* 2/2008 Sugiyama .......... A61B 1/00193
 600/114

(Continued)

*Primary Examiner* — Alexandra L Newton
*Assistant Examiner* — Rynae Boler
(74) *Attorney, Agent, or Firm* — Rahman LLC

(57) ABSTRACT

A patient monitoring, feeding, and mechanical breathing system, the system including an endotracheal probe including a first longitudinal member connected to a first camera and a semi-rigid longitudinal member inserted in an ET tube such that the first camera is aligned with a tip of the ET tube; an OG probe including a second longitudinal member configured to be inserted in an oral gastro (OG) tube, the second longitudinal member including a side camera, configured to be placed facing a window of the OG tube, wherein the side camera includes a tapered side; an enhanced OG probe, including a second camera and a motion sensor placed at the tip of the enhanced OG tube; a device communicatively coupled to the endotracheal, OG and enhanced OG probes, and having a screen configured to display images from any of the first camera, the side camera, and the second camera.

18 Claims, 17 Drawing Sheets

(56) References Cited

U.S. PATENT DOCUMENTS

| | | | |
|---|---|---|---|
| 2010/0087715 A1* | 4/2010 | Van Bommel | A61B 5/0421 |
| | | | 600/301 |
| 2014/0316198 A1* | 10/2014 | Krivopisk | A61B 1/00181 |
| | | | 600/109 |
| 2016/0151248 A1* | 6/2016 | Elia | A61J 15/0088 |
| | | | 600/547 |
| 2016/0262603 A1* | 9/2016 | Molnar | A61M 16/0666 |
| 2017/0196478 A1* | 7/2017 | Hunter | A61B 5/02055 |
| 2018/0049950 A1* | 2/2018 | Besser | A61B 1/00 |

* cited by examiner

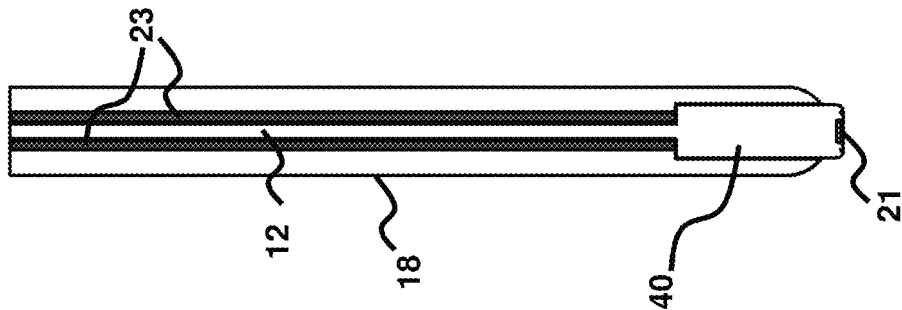
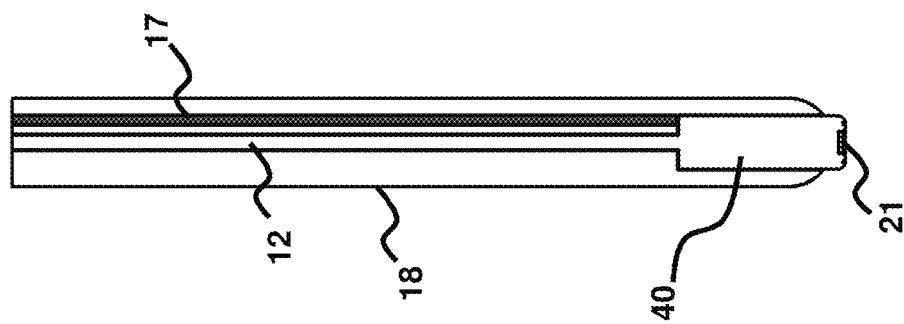
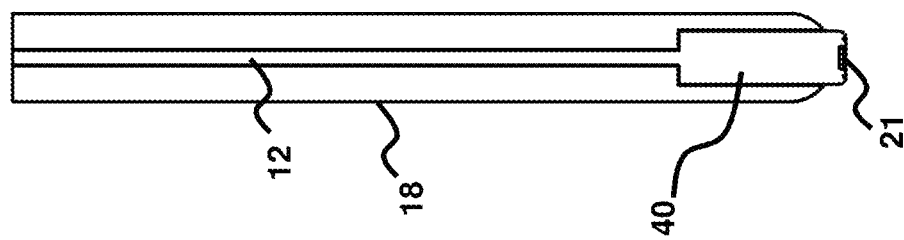
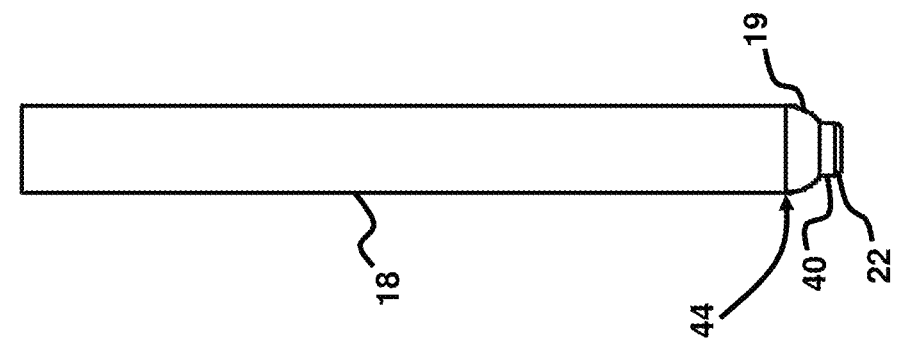

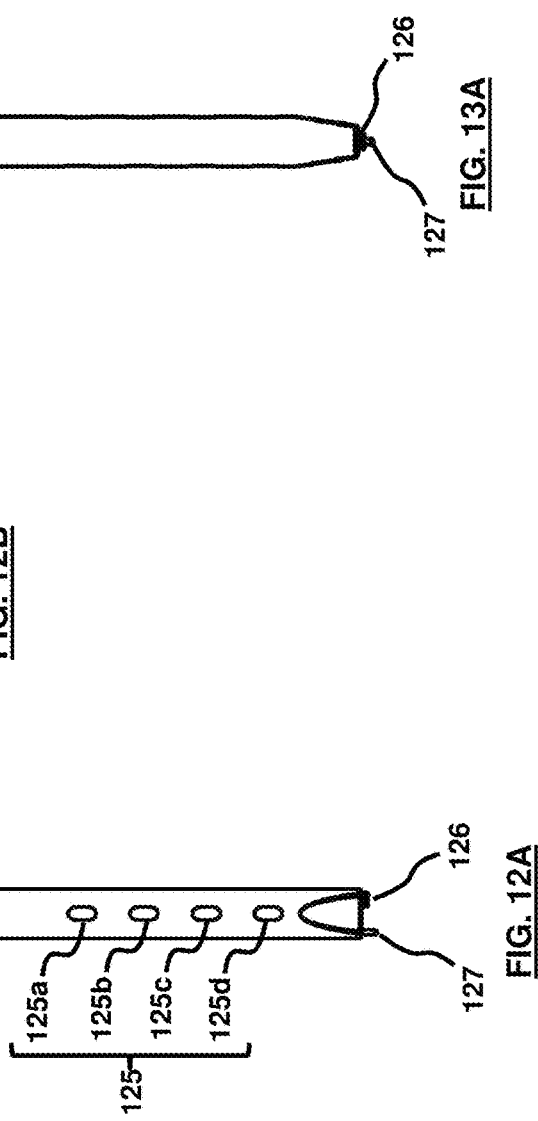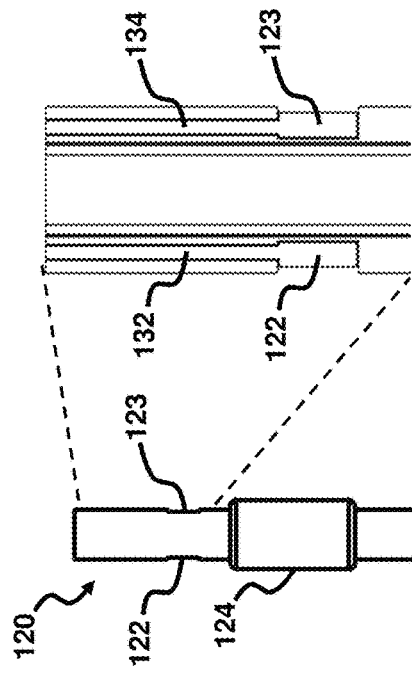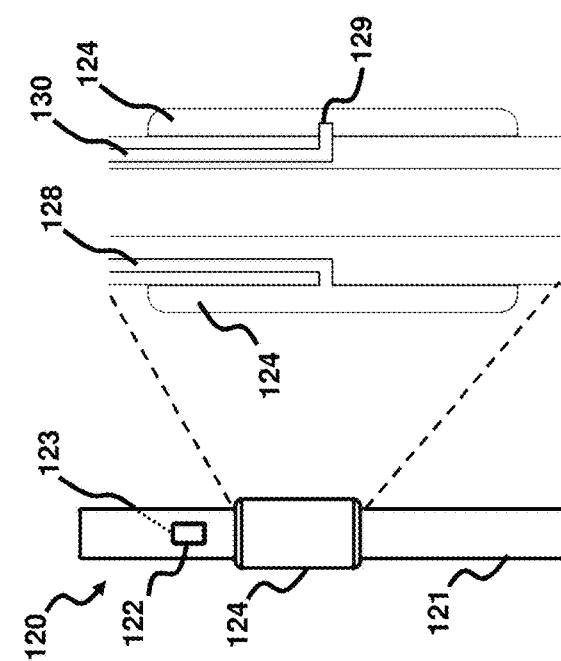

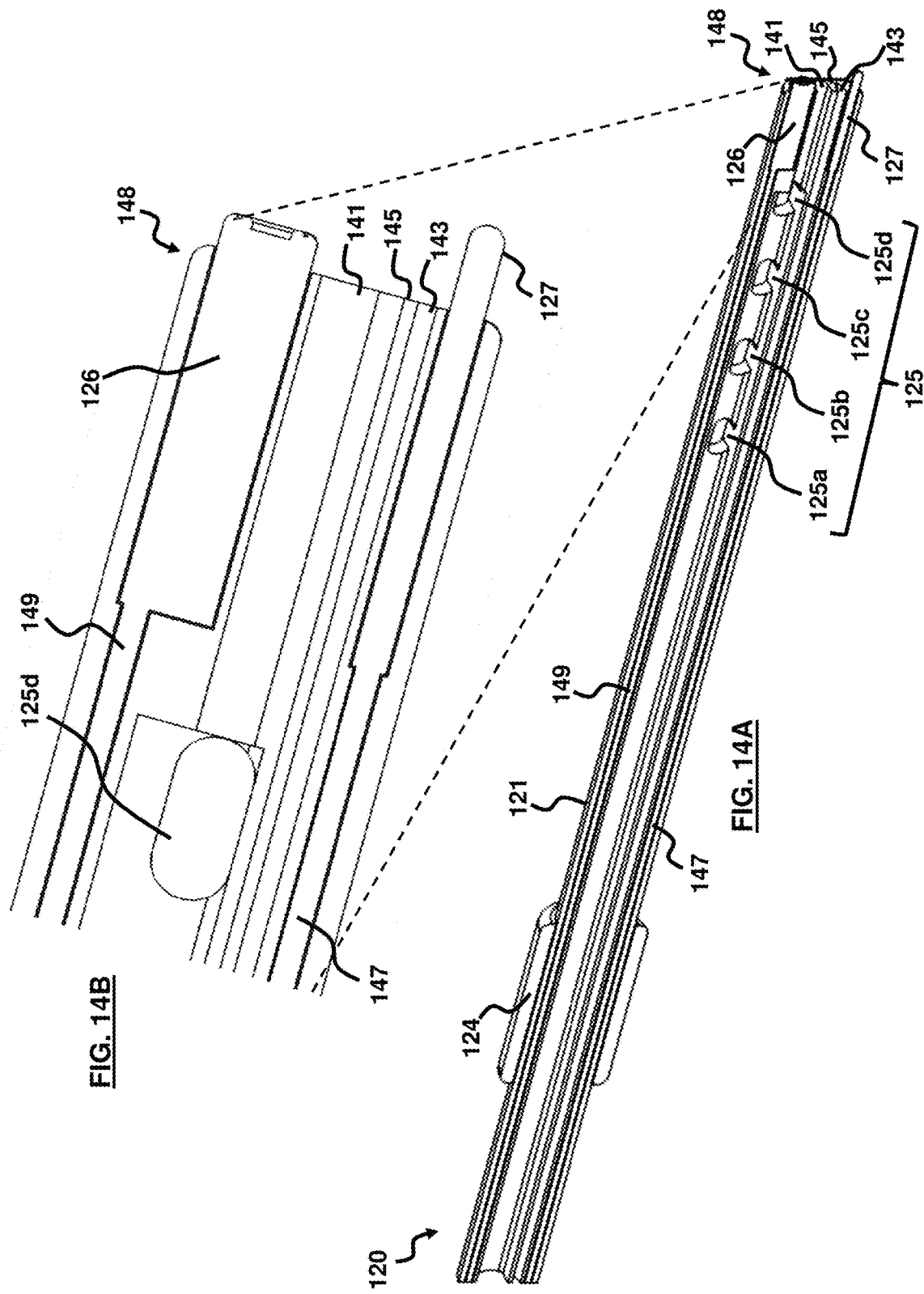

MEDICAL IMAGING SYSTEM AND DEVICE

BACKGROUND

Technical Field

The embodiments herein generally relate to medical systems, and more particularly to a medical imaging system and device.

Description of the Related Art

Taking doctors' vision beyond the skin to inside the human body without surgical incision was a major clinical challenge for the ages. The first breakthrough was in 1905 when the diagnostic X-ray was discovered. It is always desirable to provide visual and sensor assistance to doctors in placing tubes and probes inside patients' bodies.

Mechanical ventilation is provided to patients with respiratory failure through an endotracheal tube (ET) that connects a ventilator machine to the patient's lungs. Most ET tubes are approximately 30-32 cm long, with 6-9 mm of lumen diameter, made of polyvinyl chloride (PVC), and are soft in texture. The ET tube, in most cases, is placed through the mouth into the larynx and down to the trachea where it remains during a medical procedure, etc. The proper position of the ET tube tip is in the middle of the trachea. The length of the trachea in a human adult is approximately 10 cm. The procedure of ET tube placement in the trachea requires two additional tools. The first is a rigid laryngoscope that elevates the tongue and epiglottis and illuminates the pharynx area to enable the intubator to visualize the vocal cords to pass the ET tube through them into the trachea. The other tool is a semi-rigid aluminum cord (stylet), which is approximately 4 mm in diameter and 35 cm long and goes in the lumen of the soft ET tube before insertion to give it the necessary stiffness and desirable shape/curve.

The current practice of tracheal intubation allows the intubator to visualize the ET tube only until it reaches the vocal cords beyond which, the operator cannot see the tip of the ET tube. Incorrect placement of the ET tube can happen in two situations. The first is if the tube is in the esophagus and not the trachea. The second is if the ET tube tip is advanced too far into one of the two lungs. Any of these two types of incorrect placement is life threatening. Current practice requires confirming ET tube proper placement with an X-ray image.

Moreover, a patient who is unable to swallow, for example an unconscious person, might need an external feeding tube. Most commonly, a polyvinyl chloride (PVC) nasal-gastric (NG) or oral-gastro (OG) tube is used for direct delivering of nutrition or medicine to the patient's stomach. These tubes are placed blindly through the nose or the mouth into the esophagus all the way to the stomach. Incorrect placement (e.g., in the lungs) can result in life threatening complications. Conventionally, an X-ray is also required to confirm the appropriate tube placement.

SUMMARY

In view of the foregoing, an embodiment herein provides a patient monitoring, feeding, and mechanical breathing system, the system comprising an endotracheal (ET) probe comprising an ET tube comprising a hollow cylindrical body; a first longitudinal member connected to a first camera; and a semi-rigid longitudinal member operatively connected to the first longitudinal member, wherein the first longitudinal member and the semi-rigid longitudinal member are configured to be inserted in the ET tube such that the first camera is aligned with a tip of the ET tube; an oral gastro (OG) probe comprising an OG tube comprising a hollow passage; a window on the hollow passage; and a plurality of feeding holes on the hollow passage; a second longitudinal member configured to be inserted in the hollow passage, the second longitudinal member comprising a side camera, configured to be placed facing the window, wherein the side camera comprises a tapered side; an enhanced OG probe, comprising an enhanced OG tube longitudinal body; a second camera placed at a tip of the enhanced OG tube longitudinal body; and a motion sensor placed at the tip of the enhanced OG tube longitudinal body; a device communicatively coupled to the endotracheal probe, the OG probe, and the enhanced OG probe, wherein the device comprises a screen configured to display images from any of the first camera, the side camera, and the second camera.

The semi-rigid longitudinal member may comprise a semi-rigid cord operationally connected to the first camera and in parallel to the first longitudinal member. The semi-rigid longitudinal member may comprise a semi-rigid hollow cylinder operationally connected to the first camera and configured to cover the first longitudinal member. The side camera may be held in place next to the window using wax, and wherein the tapered side of the side camera is configured to assist removing the second longitudinal member from the OG tube by pulling the second longitudinal member out of the OG tube. The first camera, the side camera, and the second camera may be configured to respectively assist proper placement of the ET tube, the OG tube, and the enhanced OG tube in a patient by providing image from inside the patient.

The motion sensor of the enhanced OG tube may be configured to provide conformation of the proper placement of the enhanced OG tube in the patient by sensing a pressure applied on the patient. The enhanced OG tube may further comprise an electric sensor configured to detect an electric signal generated by a heart of the patient when the enhanced OG tube is in the patient; and generate an electrocardiogram signal to the device for generating an electrocardiogram graph of the heart of the patient on the screen. The enhanced OG tube may further comprise an audio sensor configured to detect an audio signal generated by the patient's heart when the enhanced OG tube is in the patient; and convert the audio signal to a second electrical signal and transmit the second electrical signal to the device.

The device may further comprise a speaker, and wherein the speaker regenerates a second audio signal resembling the heart audio signal using the second electrical signal. The enhanced OG tube may further comprise a balloon configured to inflate in an esophagus of a patient when the enhanced OG tube is in the patient. The enhanced OG tube may further comprise a pressure sensor inside the balloon, and wherein the pressure sensor may be configured to measure a pressure inside the esophagus of the patient when the balloon is inflated; and communicate the measurement of the pressure to the device to be displayed on the screen. The enhanced OG tube may further comprise an elongated body comprising: a first longitudinal hole configured to hold a first connector to the second camera; a second longitudinal hole configured to hold a second connector to the motion sensor; a third longitudinal hole configured to hold a third connector to the pressure sensor; a fourth longitudinal hole configured to hold a fourth connector to the electrical sensor; a fifth longitudinal hole configured to hold a fifth connector to the audio sensor; and a sixth longitudinal hole configured to create an airway to the balloon.

An embodiment herein provides a system comprising an endotracheal (ET) tube; an ET tube insert comprising a camera; a fiber optic communicatively connected to the camera; and a semi-rigid longitudinal member operationally connected to the camera, wherein the ET tube insert is configured to be inserted in the ET tube and removed while the ET tube is in a patient. The semi-rigid longitudinal member may comprise any of a semi-rigid cord and a semi-rigid hollow cylinder configured to cover the fiber optic.

An embodiment herein provides a method for inserting a tube in a patient, the method comprising providing a longitudinal member connected to a camera; inserting the longitudinal member in a tube, wherein the tube is configured to be inserted in the patient; providing a screen and a connection to the camera, wherein the screen is configured to display an image taken by the camera; inserting the tube in the patient; monitoring a location of the tube using the image; and adjusting the location of the tube in the patient using the image.

The method may further comprise removing the longitudinal member and the camera from the tube after the location of the tube is adjusted. The tube may comprise an ET tube and the camera is positioned at an opening at a tip of the ET tube. The longitudinal member may be operationally connected to a semi-rigid longitudinal member, wherein the semi-rigid longitudinal member is configured to assist the adjusting the location of the tube in the patient. The tube may comprise an OG tube, wherein the camera comprises a side camera and is placed next to a window on the OG tube, and wherein the side camera is held in place using wax. The side camera may comprise a tapered side configured to assist removing the side camera by pulling the longitudinal member when the location of the OG tube is adjusted.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3A illustrates a longitudinal member to be placed in an ET tube according to an embodiment herein;

FIG. 3B illustrates a cross-sectional view of a longitudinal member to be placed in an ET tube according to an embodiment herein;

FIG. 3C illustrates a cross-sectional view of a longitudinal member to be placed in an ET tube according to an embodiment herein;

FIG. 3D illustrates a cross-sectional view of a longitudinal member to be placed in an ET tube according to an embodiment herein;

FIG. 12A illustrates an enhanced OG tube according to an embodiment herein;

FIG. 12B illustrates a section of an enhanced OG tube according to an embodiment herein;

FIG. 13A illustrates an enhanced OG tube according to an embodiment herein;

FIG. 13B illustrates an enhanced OG tube according to an embodiment herein;

FIG. 14A illustrates a longitudinal cross-section of an enhanced OG tube according to an embodiment herein;

FIG. 14B illustrates a longitudinal cross-section of a section of an enhanced OG tube according to an embodiment herein;

DETAILED DESCRIPTION

Figure 1:
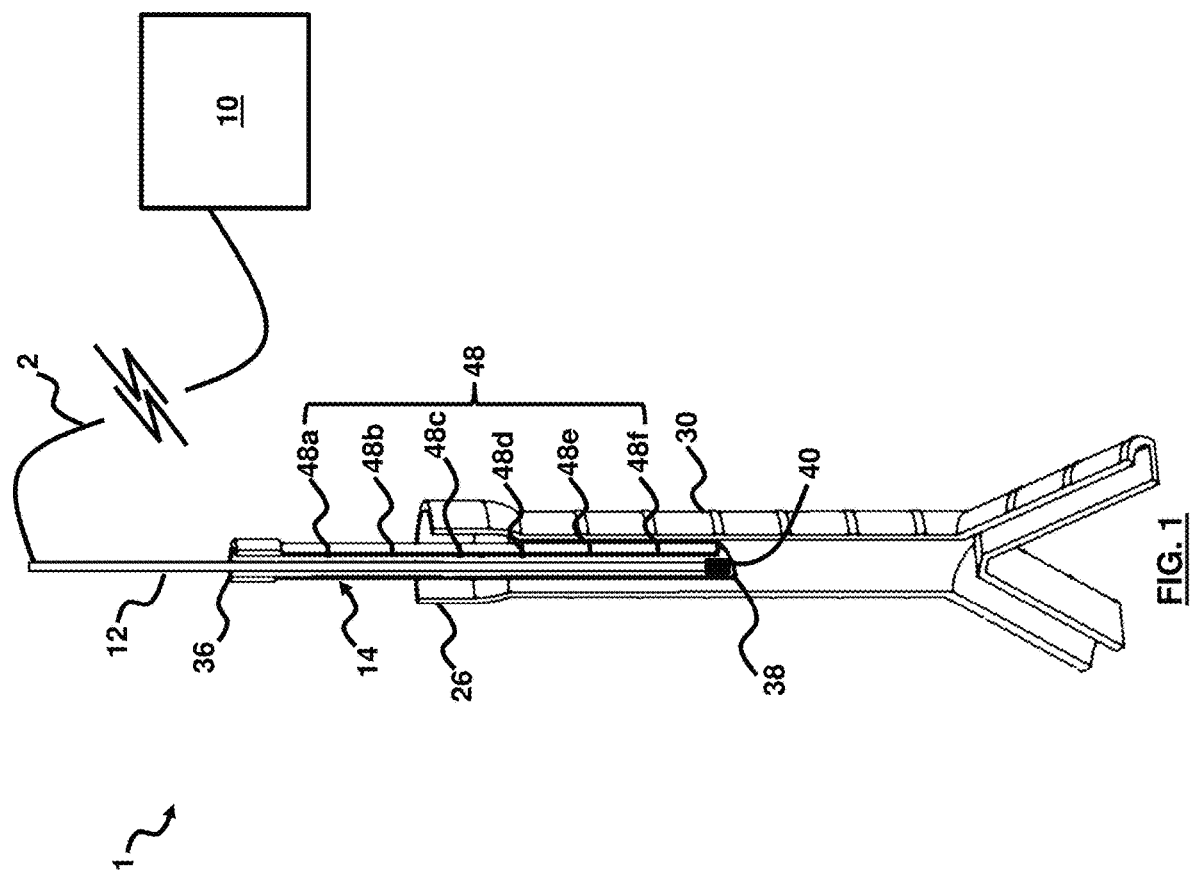
FIG. 1 illustrates a system for placing and locating an ET tube according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Some embodiments herein provide an ET tube probe that uses a camera system to allow for proper ET tube placement. ET tubes may be made of PVC and are generally soft and flexible. However, for the ET tube to properly advance through the mouth and larynx, it needs to have certain degree of firmness or rigidity. Some embodiments herein use a semi rigid aluminum cord (a stylet) in the ET tube to increase its rigidity. The stylet may easily bend and take new shapes even while it is inside the ET tube.

Some embodiments herein provide an OG tube probe that uses a camera system to allow for proper ET tube placement. Some embodiments herein provide an OG tube probe that uses a side camera system to help proper placement of the OG tube inside the patient's stomach, and a pressure sensor that allows for confirmation of the proper placement of the OG tube. An embodiment herein uses a microphone system and an electrical sensor in an OG tube to also allow for monitoring heartbeat of a patient. An embodiment herein uses a pressure sensor inside a balloon to measure pressure inside a patient's body.

An embodiment herein provides a display configured to receive multiple video and one audio signals from probes inside a patient body. In an embodiment, visual signal from tracheal intubation is displayed.

Referring now to the drawings, and more particularly to FIGS. 1 through 17, where similar reference characters denote corresponding features consistently throughout the figures, there are shown preferred embodiments.

FIG. 1 illustrates a probe system 1 configured to identify a proper placement of an ET tube 14 that is placed inside the larynx 26 and trachea 30 of a human body, according to an embodiment herein. The system 1 may comprise a first longitudinal member 12 and a tube 14. The first longitudinal member 12 comprises a camera 40. The first longitudinal member 12 may provide any of mechanical, electronic, or optical connection 2 to the camera 40. In an embodiment the first elongated member 12 comprises an optical fiber. The camera 40 may be connected to a display 10 via a connection 2. Connection 2 may be a wired or a wireless connection. The first longitudinal member 12 is configured to be inserted into an ET tube 14 that is configured to be inserted in the larynx 26 and down to the trachea 30, in an embodiment herein. The ET tube 14 comprises a first end 36 and an oppositely positioned second end 38. The second end 38 may be an angled tip. The camera 40 may be positioned at the second end 38 of the ET tube 14. The ET tube 14 may be marked by positional indicators 48a, 48b, 48c, 48d, 48e, 48f, collectively referred to herein as positional indicators 48. In an embodiment, positional indicators 48a-48f may be spaced apart 1 cm from each other. In an embodiment, positional indicators 48 may include sufficient number of markings that cover the ET tube 14 with 1 cm intervals.

Figure 2:
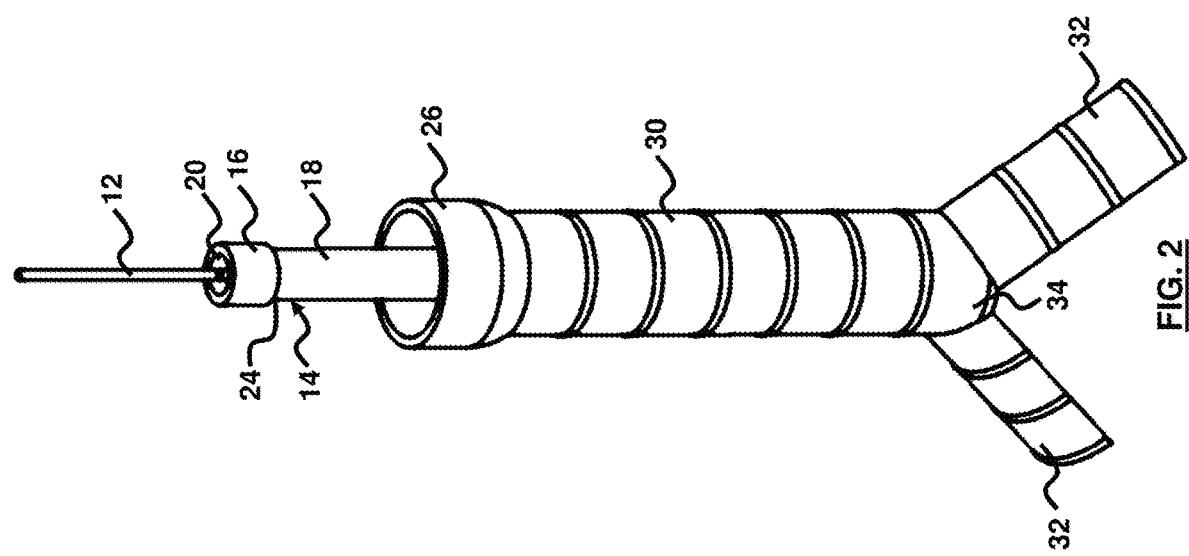
FIG. 2 illustrates placing and locating an ET tube according to an embodiment herein.

FIG. 2, with reference to FIG. 1, illustrates the first longitudinal member 12 inserted into the ET tube 14 inserted into the larynx 26 and trachea 30. The trachea 30 terminates at the carina 34 before splitting to the bronchi 32. The ET tube 14 may be conventionally configured and comprises a hollow upper portion 16 that leads to an elongated portion 18. A lip 24 is configured between the confluence of the upper portion 16 and elongated portion 18. The upper portion comprises an opening 20 to permit the first longitudinal member 12 to be inserted and retracted in/from the ET tube 14.

In an embodiment, the first longitudinal member 12 is placed in the ET tube 14, before the ET tube 14 is inserted in the human body, and the first longitudinal member 12 and the ET tube 14 are inserted into the human body together. In an embodiment, the first longitudinal member 12 is placed in the ET tube 14 such that the camera 40 is aligned with the second end 38, before the ET tube 14 is inserted in the human body. In an embodiment, the first longitudinal member 12 is attached to the ET tube 14. In an embodiment, the first longitudinal member 12 is freely movable relative to the ET tube 14. The first longitudinal member 12 may be removable from the ET tube 14.

The camera 40 is configured to transmit the image of inside the trachea 30 to the display 10 using the connection 2. Using the image displayed on the display 10, an operator can determine when the second end 38 in the middle of the trachea 30, or at a specific distance from the carina 34.

The larynx 26 provides for a better placement marker than a patient's lips (as in the conventional medical practice) because from the larynx 26 to the middle of the trachea 30 is only approximately 5 cm, with no anatomical variations therebetween. In use, after the ET tube 14 is introduced into the trachea 30, the first longitudinal member 12 is introduced into the ET tube 14 until the second end 38 of the first longitudinal member 12 reaches the level of the carina 34. The operator, using the image transmitted from the camera 40 to the display 10, determines when the second end 38 of the first longitudinal member 12 reaches the level of the carina 34. Then, using the positional indicators 48, the ET tube 14 is brought 5 cm outside the larynx 26. This ensures the second end 38 of the ET tube 14 to be in the middle of the trachea 30 (e.g., trachea is approximately 10 cm in length).

In an embodiment, an X-ray may be used to confirm the proper placement of the ET tube 14. However, the embodiments herein provide a technique to eliminate the guesswork involved in determining whether an ET tube 14 has been properly placed inside a patient, and also eliminate the need for multiple time-consuming and costly X-rays in order to confirm this proper placement.

FIGS. 3A-3D, with reference to FIGS. 1 and 2, are schematic diagrams illustrating the first longitudinal member 12 attached to an ET insert 18, according to some embodiments herein. FIG. 3A illustrates exterior of the ET tube insert 18, and the camera 40 operationally attached to the ET tube insert 18 via a tapered connector 19. The camera 40 may be covered with a glass layer 22. FIG. 3B is a schematic diagram illustrating the first longitudinal member 12 inside the ET tube insert 18. The camera 40 includes a first lens 21, according to an embodiment herein.

FIG. 3C is a schematic diagram illustrating the ET tube insert 18 comprising the first longitudinal member 12 and a semi-rigid cord 17 inside the ET tube insert 18. The semi-rigid cord 17 provides enough rigidity for an operator to guide the ET tube 14 and the ET tube insert 18 in the larynx 26 and into the trachea 30. In an embodiment, the semi-rigid cord 17 comprises aluminum.

FIG. 3D is a schematic diagram illustrating the ET tube insert 18 comprising the first longitudinal member 12 and a semi-rigid hollow cylinder 23, configured to cover the longitudinal member 12 inside the ET tube insert 18. The semi-rigid hollow cylinder 23 provides enough rigidity for an operator to guide the ET tube 14 and the ET tube insert 18 in the larynx 26 and into the trachea 30. In an embodiment, the semi-rigid hollow cylinder 23 has a hollow cylindrical shape that covers the first longitudinal member 12. In an embodiment, the semi-rigid hollow cylinder 23 comprises aluminum.

Figure 4B:
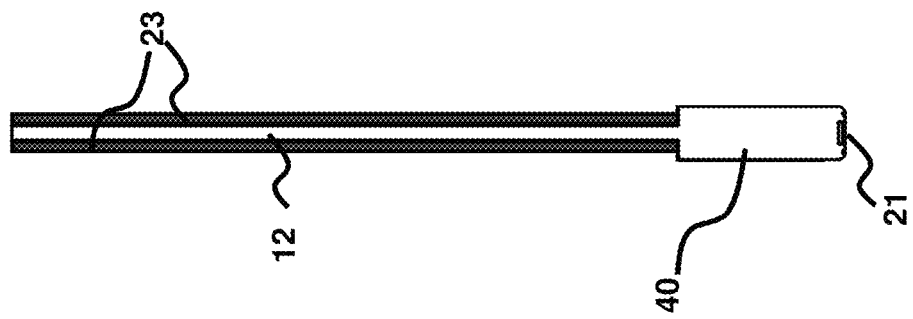
FIG. 4B illustrates a longitudinal member to be placed in an ET tube according to an embodiment herein.
Figure 4A:
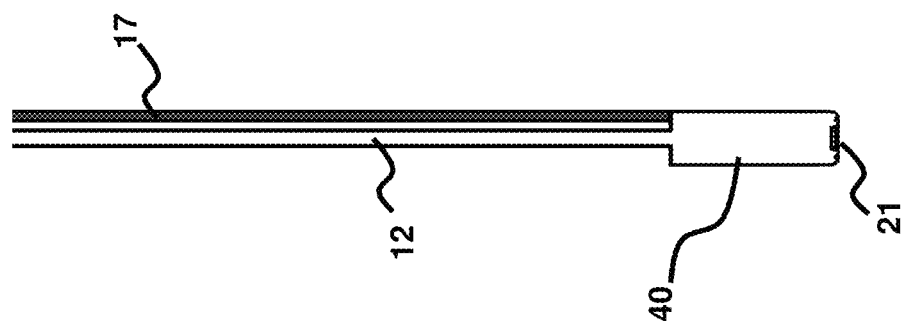
FIG. 4A illustrates a longitudinal member to be placed in an ET tube according to an embodiment herein.

FIG. 4A, with reference to FIGS. 1 through 3D, is a schematic diagram illustrating the first longitudinal member 12 with the semi-rigid cord 17, according to an embodiment herein. In an embodiment, only the first longitudinal member 12, the camera 40, and the semi-rigid cord 17 may be directly inserted in the ET tube 14. The semi-rigid cord 17 provides enough rigidity for an operator to guide the ET tube 14 and the first longitudinal member 12 in the larynx 26 and into the trachea 30.

FIG. 4B, with reference to FIGS. 1 through 4A, is a schematic diagram illustrating the first longitudinal member 12 with the semi-rigid hollow cylinder 23, according to an embodiment herein. In an embodiment, only the first longitudinal member 12, the camera 40, and the semi-rigid hollow cylinder 23 may be directly inserted in the ET tube 14. The semi-rigid cord 17 provides enough rigidity for an operator to guide the ET tube 14 and the first longitudinal member 12 in the larynx 26 and into the trachea 30.

Figure 5B:
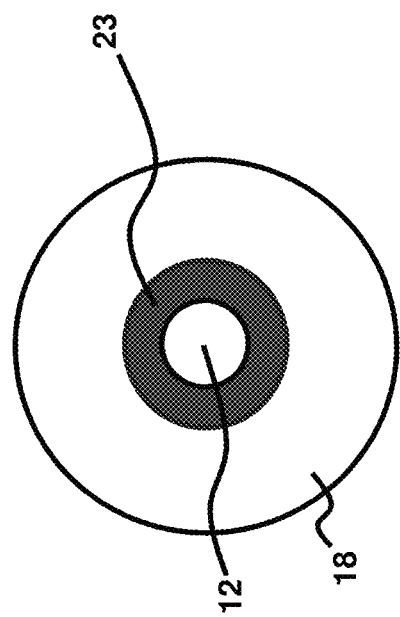
FIG. 5B illustrates a cross-section of a longitudinal member to be placed in an ET tube according to an embodiment herein.
Figure 5A:
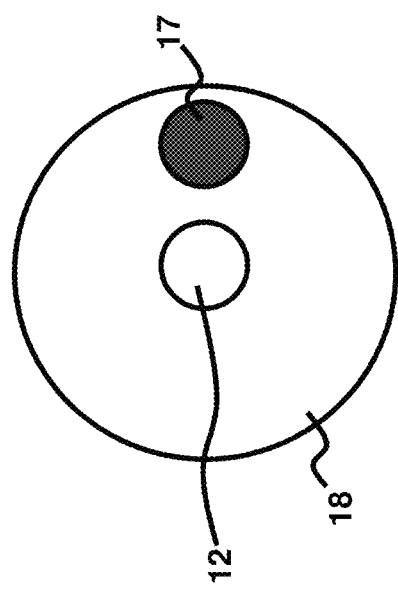
FIG. 5A illustrates a cross-section of a longitudinal member to be placed in an ET tube according to an embodiment herein.

FIG. 5A, with reference to FIGS. 1 through 4B, is a schematic diagram illustrating a cross-section of the ET tube insert 18 including the first longitudinal member 12 and the semi-rigid cord 17, according to an embodiment herein. FIG. 5B, with reference to FIGS. 1 through 5A, is a schematic diagram illustrating a cross-section of the ET tube insert 18 including the first longitudinal member 12 and the semi-rigid hollow cylinder 23, according to an embodiment herein.

Figure 6:
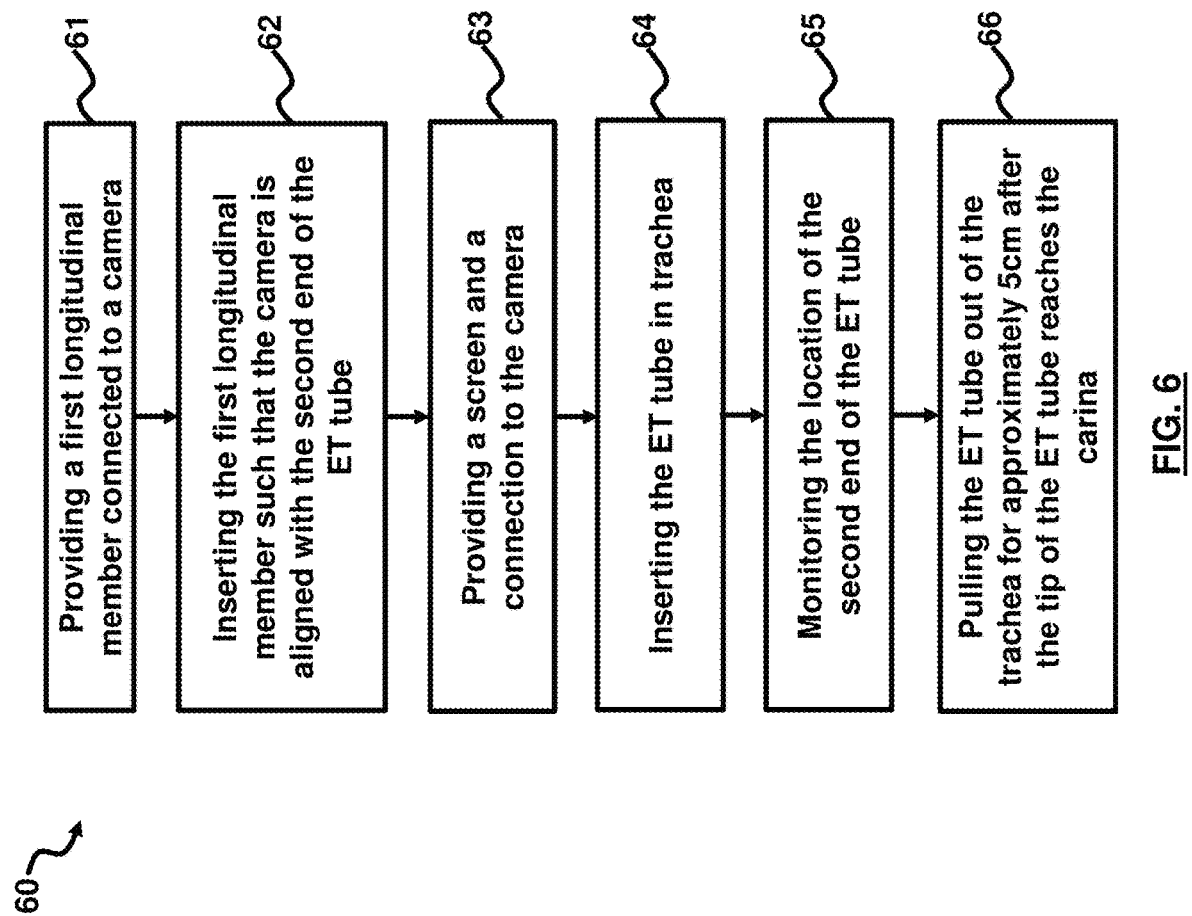
FIG. 6 is a flowchart illustrating a method for proper placement of an ET tube according to an embodiment herein.
Figure 7:
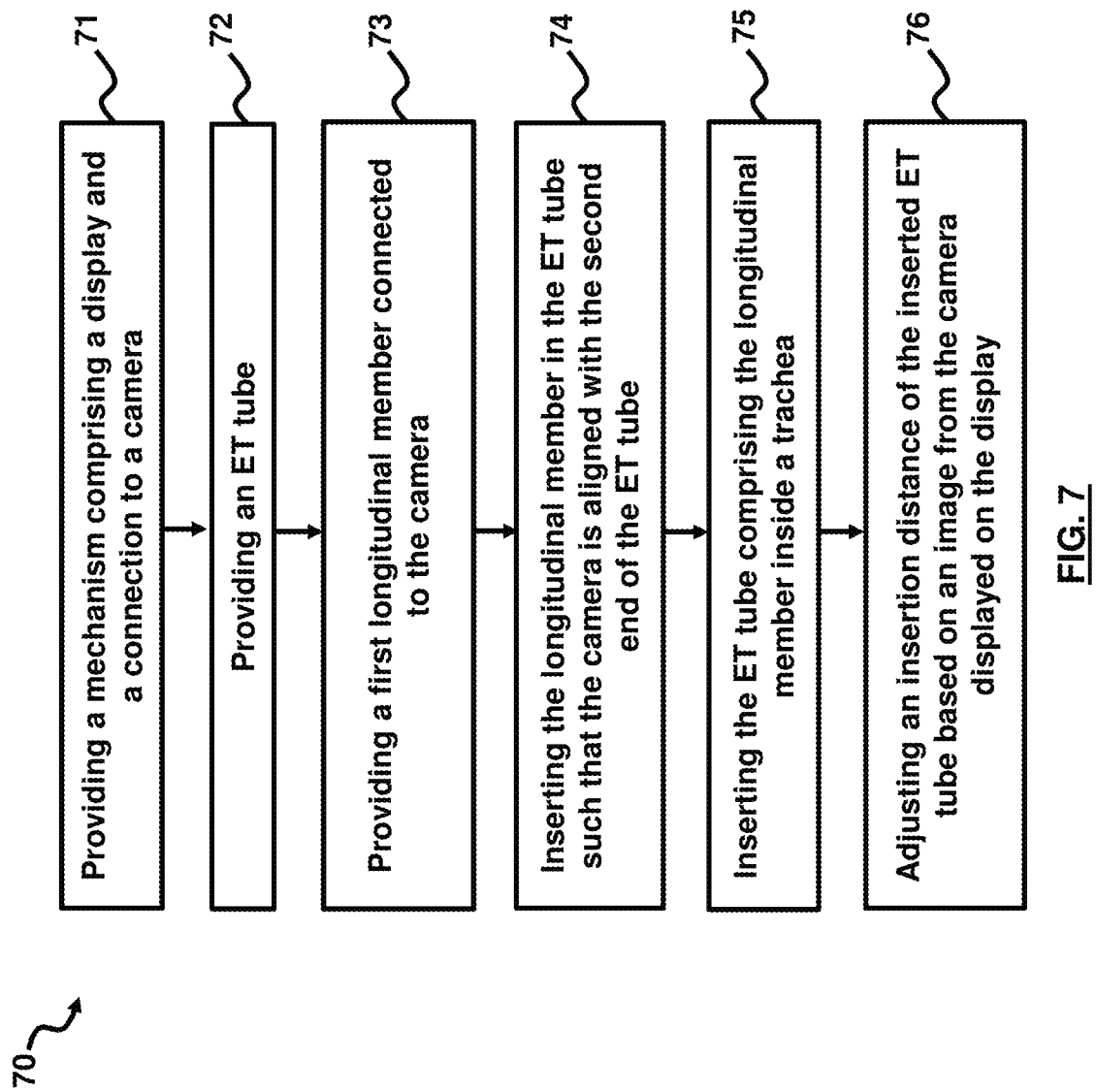
FIG. 7 is a flowchart illustrating a method for proper placement of an ET tube according to an embodiment herein.

FIGS. 6 and 7, with reference to FIGS. 1 through 5B, illustrate flow diagrams according to the embodiments herein. As shown in FIG. 6, a method 60 of identifying the proper placement of the ET tube 14 that is placed inside a human body (e.g., larynx 26 and trachea 30) is provided according to an embodiment herein. The method comprises providing (61) a first longitudinal member 12 connected to a camera 40; inserting (62) the first longitudinal member 12 such that the camera 40 is aligned with the second end 38 of the ET tube 14; providing (63) a screen 10 and a connection 2 to the camera 40; inserting (64) the ET tube 14 in trachea 30; monitoring (65) the location of the second end 38 of the ET tube 14; and pulling (66) the ET tube 14 out of the trachea 30 for approximately 5 cm after the second end 38 of the ET tube 14 reaches the carina 34.

As shown in FIG. 7, a method 70 of identifying the proper placement of the ET tube 14 that is placed inside a human body (e.g., larynx 26 and trachea 30) is provided according to an embodiment herein. The method comprises providing (71) a mechanism comprising a display 10 and a connection 2 to a camera 40; providing (72) an ET tube 14; providing (73) a first longitudinal member 12 connected to the camera 40; inserting (74) the longitudinal member 12 in the ET tube 14 such that the camera 40 is aligned with the second end 38 of the ET tube 14; inserting (75) the ET tube 14 comprising the longitudinal member 12 inside a trachea 30; and adjusting (76) an insertion distance of the inserted ET tube 14 based on an image from the camera 40 displayed on the display 10.

Figure 8:
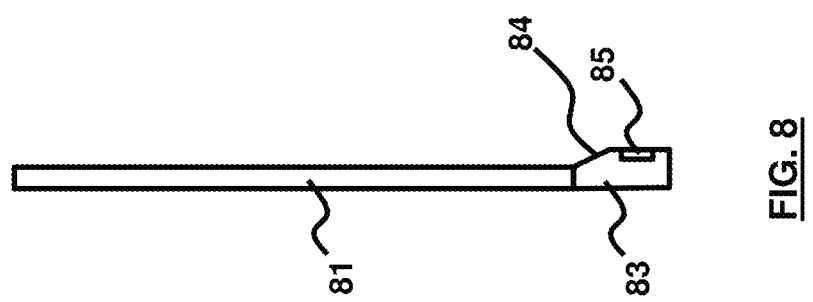
FIG. 8 illustrates a longitudinal member to be placed in an OG tube according to an embodiment herein.

FIG. 8, with reference to FIGS. 1 through 7, is a schematic diagram illustrating a second longitudinal member 81 communicatively coupled to a side camera 83, according to an embodiment herein. The side camera 83 includes a second lens 85. In an embodiment, a side 84 of the camera 83, where the camera 83 is connected to the second longitudinal member 81, is tapered. The longitudinal member 81 may provide any of mechanical, electronic, or optical connection to the side camera 83. In an embodiment the second elongated member 81 comprises an optical fiber. The side camera 83 may be connected to the display 10 via a connection 2, as illustrated in FIG. 1.

FIG. 9A is a schematic diagram illustrating an oral gastric (OG) tube 102, according to an embodiment herein. The OG tube 102 is configured to be inserted into the pharynx and down to the esophagus into the stomach for feeding a patient. The OG tube 102 may comprise a first hollow passage 106 and a second hollow passage 108. The OG tube 102 may further comprise feeding holes 104a, 104b, 104c, and 104d connected to the hollow passage 106. The OG tube 102 may have any number of feeding holes. The first OG tube 102 may be configured to receive the second longitudinal member 81 in the hollow passage 106.

Figure 9:
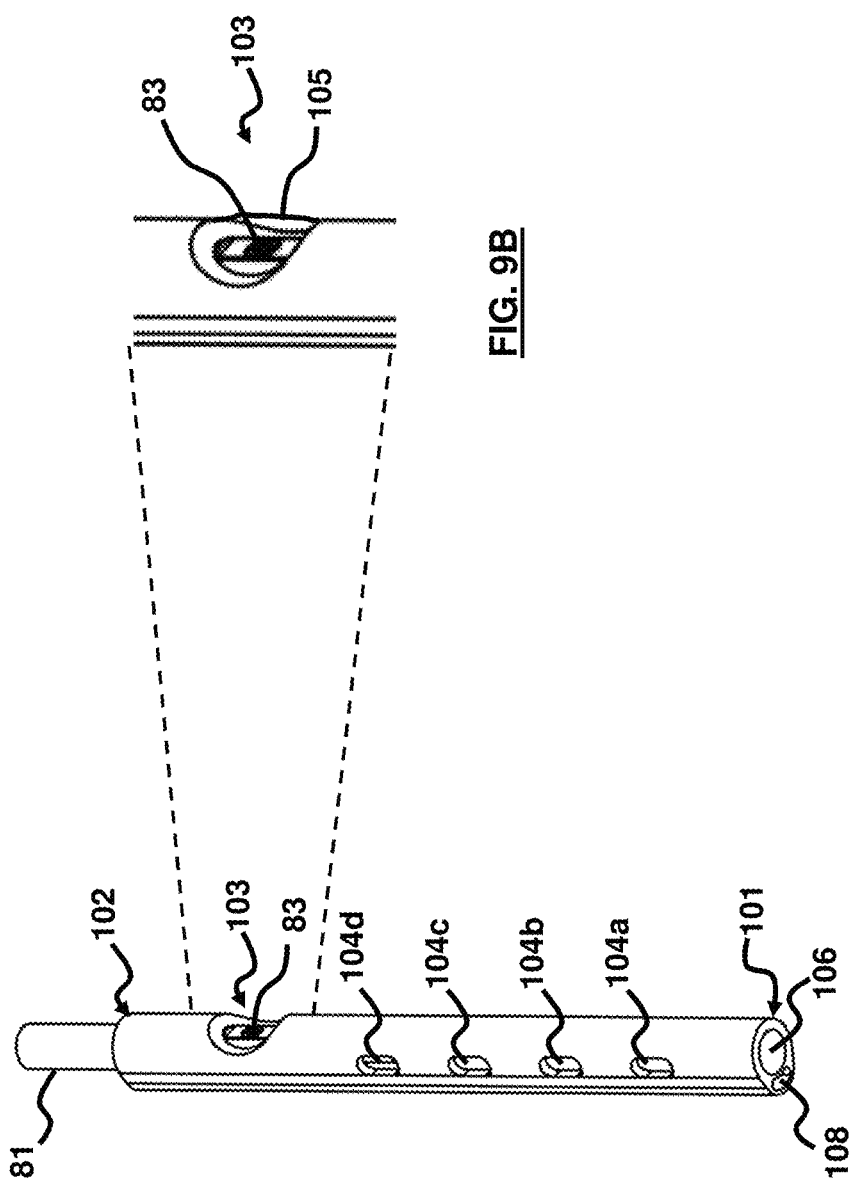
FIG. 9A illustrates a longitudinal member placed in an OG tube according to an embodiment herein.
FIG. 9B illustrates a longitudinal member placed in an OG tube according to an embodiment herein.

The side camera 83 may be configured to be positioned aligned with a window 103 of the OG tube 102 when the second longitudinal member 81 is inserted in the OG tube 102. FIG. 9B, with reference to FIGS. 1 through 9A, illustrates an enlarged section of the OG tube 102 including the window 103 with the camera 83 positioned in place. In an embodiment, the camera 83 is held in place using medical wax 105. The medical wax 105 may be added to keep the camera 83 in place after the camera 83, connected to the second longitudinal member 81, is placed in front of the window 103.

In an embodiment, after the OG tube 102 with the second longitudinal member 81 is inserted in the patient's stomach, the side camera 83 is used to determine and adjust the right position for the OG tube 102, and then the second longitudinal member 81 and the camera 83 are removed from the OG tube 102. The tapered side 84 of the camera 83 provides for conveniently removing the second longitudinal member 81 and the camera 83, after it is held in place using the medical wax 105. This convenience of removal is because of the less friction caused by the tapered side 84 with the medical wax 105.

Figure 10:
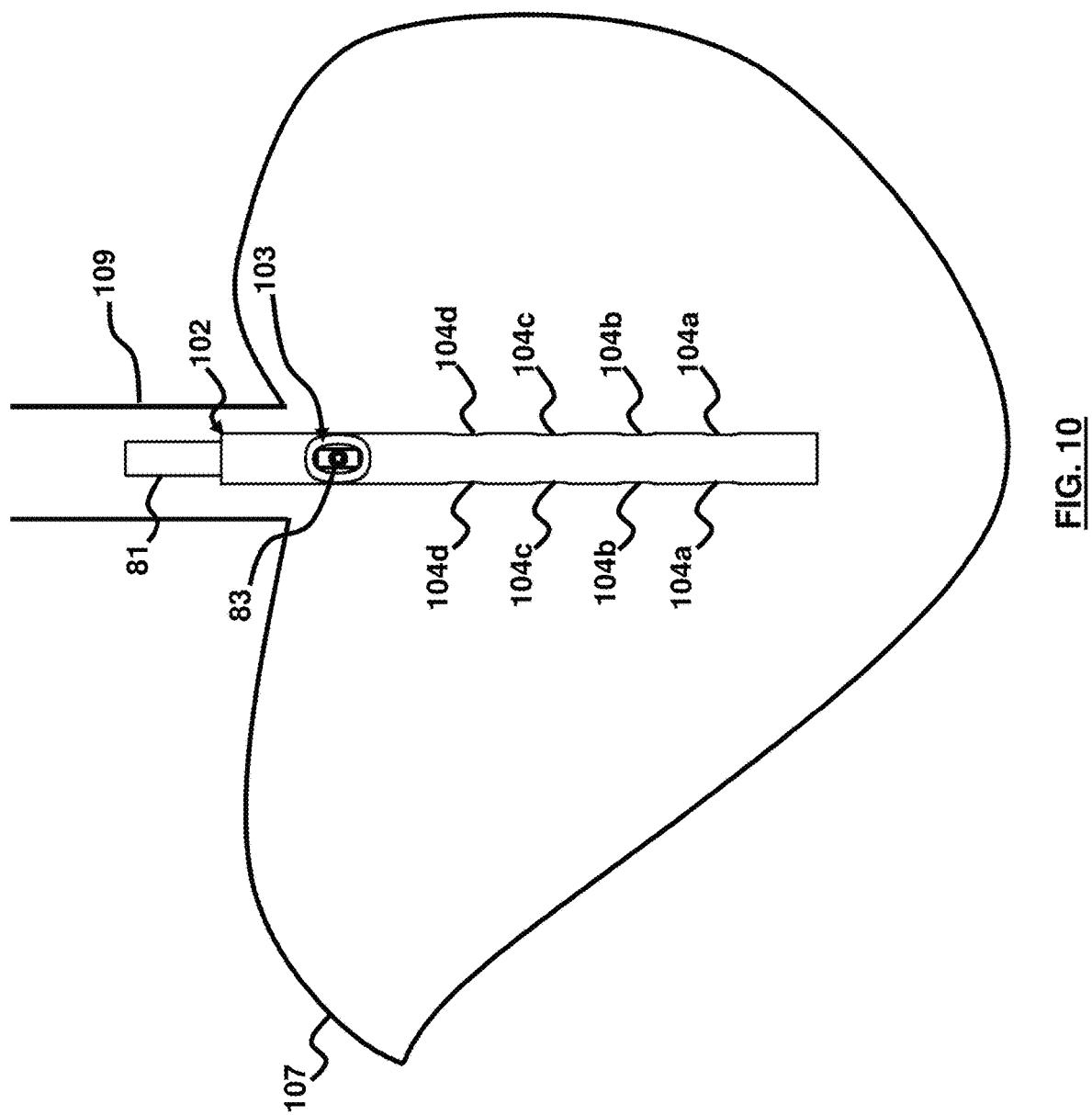
FIG. 10 illustrates an OG tube inserted in a patient's stomach according to an embodiment herein.

FIG. 10, with reference to FIGS. 1 through 9B, is a schematic diagram illustrating the OG tube 102, having the second longitudinal member 81 and the camera 83 inserted in and in place, inside a stomach 107.

In an embodiment, the feeding holes 104a-104d are placed inside the stomach 107, and the window 103 is placed inside the stomach 107, right below the esophagus 109. While inserting the OG tube 102 in the esophagus 109, the camera 83 is used to determine the correct positioning of the OG tube 102. In an embodiment, after the camera 83 determines that the window 103 has passed the esophagus 109 and has entered the stomach 107, the correct positioning of the OG tube 102 is reached. In an embodiment, upon detecting cartilage rings in the esophagus 109 by the camera 83 it is an indication that the window 103 is in the esophagus 109. When the camera 83 does not detect the cartilage rings in the esophagus 109, and instead the inner wall of the stomach 107 is detected by the camera 83, and is displayed on the screen 10, the operator will know that the window 103 is inside the stomach 107 and the correct positioning of the OG tube 102 has occurred.

FIG. 10 further illustrates a front view of the first OG tube 102, with the window 103, the feeding holes 104a-104d. In an embodiment herein, the feeding holes 104a-104d may extend across the OG tube 102.

Again with reference to FIG. 9A, in an embodiment herein, the tip 101 of the OG tube 102 is cut and smoothened out. Then the first longitudinal member 12 connected to the camera 40 is inserted in the OG tube 102 such that the camera 40 is aligned with the tip 101 of the OG tube 102. The camera 40 is then held in placed, aligned with the tip 101, using medical wax 105.

Figure 11:
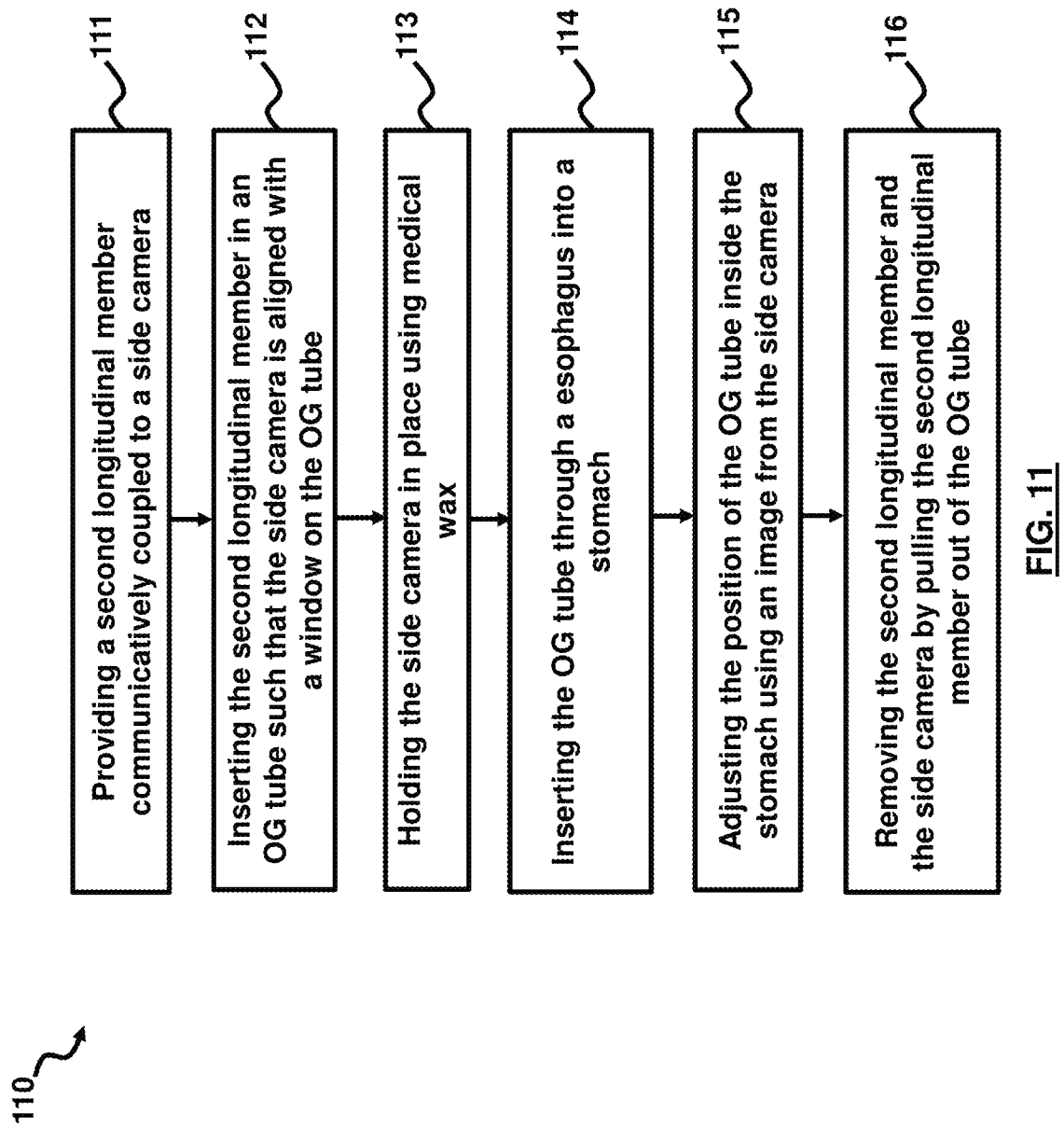
FIG. 11 is a flowchart illustrating a method for proper placement of an OG tube according to an embodiment herein.

FIG. 11, with reference to FIGS. 1 through 10, illustrates a flow diagram according to the embodiments herein. As shown in FIG. 11, a method 110 of identifying the proper placement of the OG tube 102 that is placed inside a human body (e.g., esophagus 109 and stomach 107) is provided according to an embodiment herein. The method comprises providing (111) a second longitudinal member 81 communicatively coupled to a side camera 83; inserting (112) the second longitudinal member 81 in an OG tube 102 such that the side camera 83 is aligned with a window 103 on the OG tube 102; holding (113) the side camera 83 in place using medical wax 105; inserting (114) the OG tube 102 through a esophagus 109 into a stomach 107; adjusting (115) the position of the OG tube 102 inside the stomach 107 using an image from the side camera 83; and removing (116) the second longitudinal member 81 and the side camera 83 by pulling the second longitudinal member 81 out of the OG tube 102.

FIGS. 12A-12B, with reference to FIGS. 1 through 11, are schematic diagrams illustrating an enhanced OG tube 120 and different sections of the enhanced OG tube 120, according to some embodiments herein.

FIG. 12A illustrates the enhanced OG tube 120, including a longitudinal body 121. The enhanced OG tube 120 may further include an electrical sensor 122, and an audio sensor 123 located the opposite side of the electrical sensor 122 on the longitudinal body 121. The enhanced OG tube 120 may further include a balloon 124, and feeding holes 125a, 125b, 125c, and 125d (collectively referred to herein as the feeding holes 125) according to an embodiment herein. The enhanced OG tube 120 may include any number of feeding holes. The enhanced OG tube 120 may further include a camera 126 and a motion sensor 127.

FIG. 12B is a schematic diagram illustrating an enlarged section of the balloon 124 and the enhanced OG tube 120 underneath the balloon 124, according to an embodiment herein. The enhanced OG tube 120 may include an air passage 128 configured to facilitate an air flow for inflating the balloon 124 to touch the interior wall of the esophagus 109, once the enhanced OG tube 120 is inserted in a patient's stomach 107. The enhanced OG tube 120 further comprises a pressure sensor 129 communicatively coupled to a pressure sensor connector 130. The pressure sensor 129 is configured to measure the pressure inside the patient's esophagus 109, once the enhanced OG tube 120 is inserted inside the patient's stomach 107. The pressure sensor 124 may be connected to a pressure sensor connector 130.

FIG. 13A is a schematic diagram illustrating a side view of the enhanced OG tube 120, including the longitudinal body 121, the electrical sensor 122, the audio sensor 123, the balloon 124, the camera 126, and the motion sensor 127, according to an embodiment herein. FIG. 13B is a schematic diagram illustrating an enlarged section of a portion of the enhanced OG tube 120 that includes the electrical sensor 122 and the audio sensor 123, according to an embodiment herein. The electrical sensor 122 may be connected to the electrical sensor connector 132, and the audio sensor 123 may be connected to an audio sensor connector 134.

FIGS. 14A and 14B, with reference to FIGS. 1 through 13B, are schematic diagrams illustrating a longitudinal cross-section of the enhanced OG tube 120, according to an embodiment herein. FIG. 14A is a schematic diagram illustrating longitudinal cross-section of the enhanced OG tube 120 including the balloon 124, the longitudinal member 121, the feeding holes 125, the camera 126, and the motion sensor 127. The enhanced OG tube 120 may further include a first enhanced OG hollow passage 141 connected to the feeding holes 125, and a second enhanced OG hollow passage 143. A wall 145 may separate the first hollow passage 141 and the second hollow passage 143. The camera 141 may be connected to a camera connector 149, and the motion sensor may be connected to a motion sensor connector 147.

FIG. 14B is a schematic diagram illustrating an enlarged longitudinal cross-section of the enhanced OG tube 120 near the enhanced OG tip 148 that includes the camera 126 and the motion sensor 127, according to an embodiment herein.

Figure 15A:
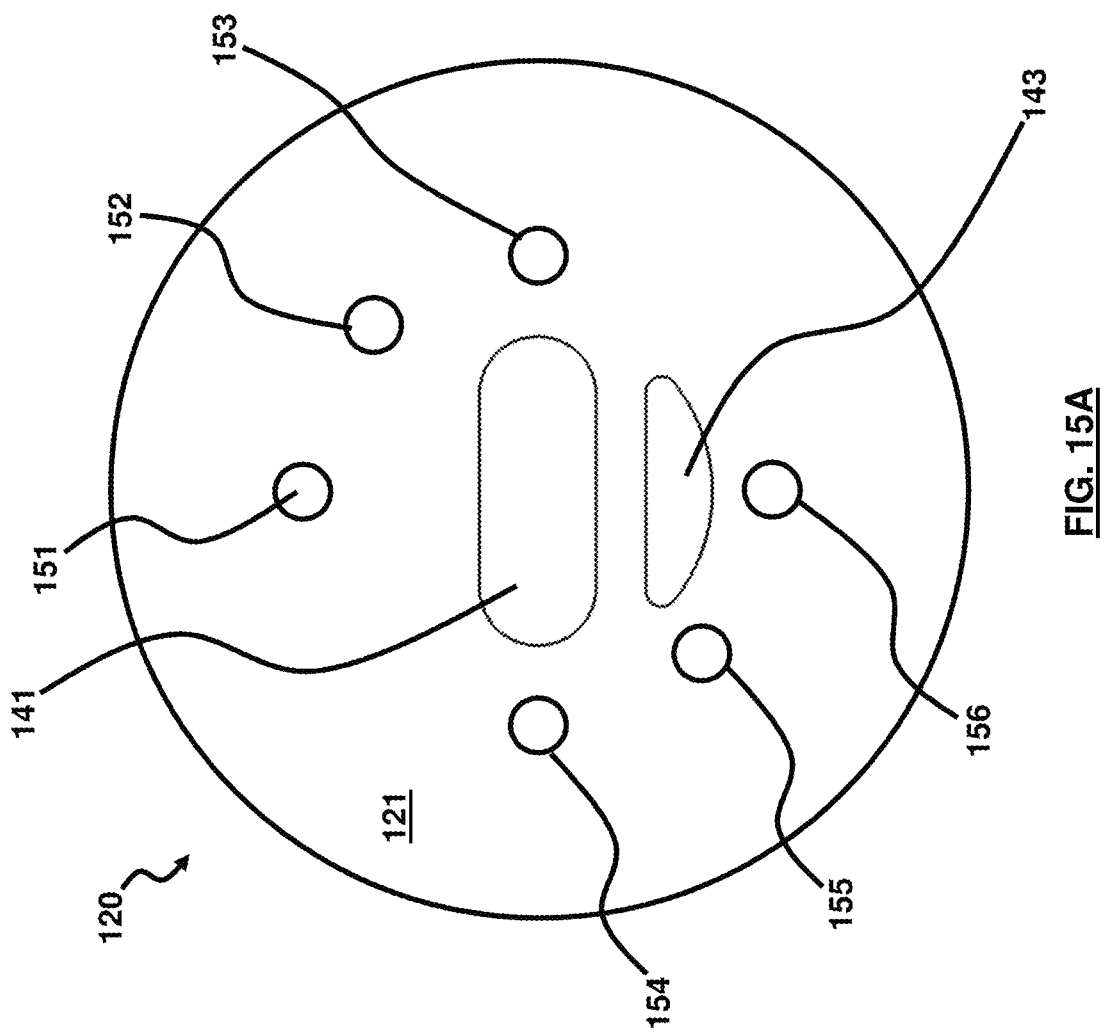
FIG. 15A illustrates a cross-section of an enhanced OG tube according to an embodiment herein.
Figure 15B:
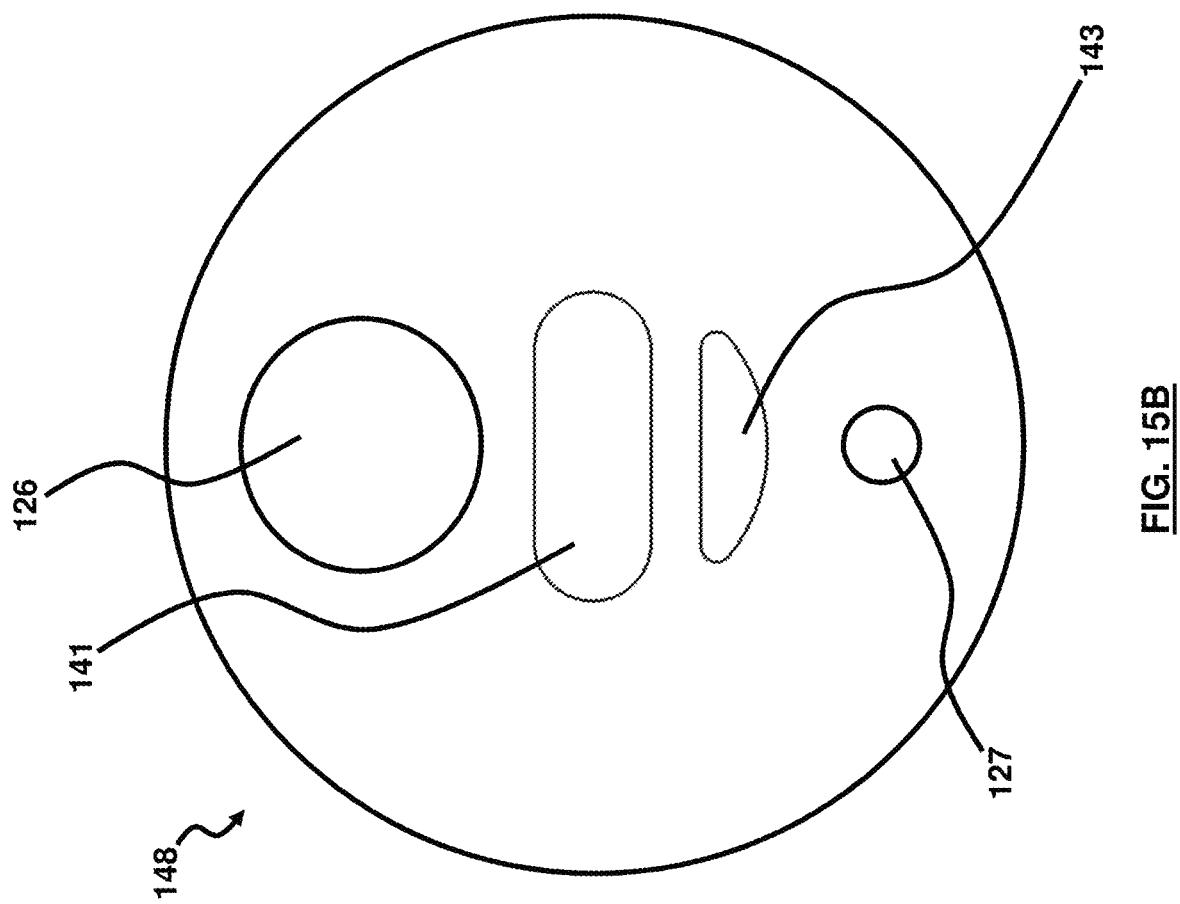
FIG. 15B illustrates a cross-section of an enhanced OG tube according to an embodiment herein.

FIGS. 15A and 15B, with reference to FIGS. 1 through 14B, are schematic diagrams illustrating cross-sections of the enhanced OG tube 120, according to an embodiment herein. FIG. 14A is a schematic diagram illustrating the cross-section of the enhanced OG tube 120 near the top of the OG tube 120 (above the electrical sensor 122 and the acoustic sensor 123 in FIG. 12A). The longitudinal body 121 of the enhanced OG tube 120 may include longitudinal holes 151, 152, 153, 154, 155, and 156 configured to house the electrical sensor connector 132, the acoustic sensor connector 134, the air flow passage 128, the pressure sensor connector 124, the camera connector 149, and the motion sensor connector 147, respectively. FIG. 15B is a schematic diagram illustrating the enhanced OG tip 148 including the camera 126 and the motion sensor 127, according to an embodiment herein. The first hollow passage 141 and the second hollow passage 143 may connect the two ends of the enhanced OG tube 120, according to an embodiment herein.

Figure 16:
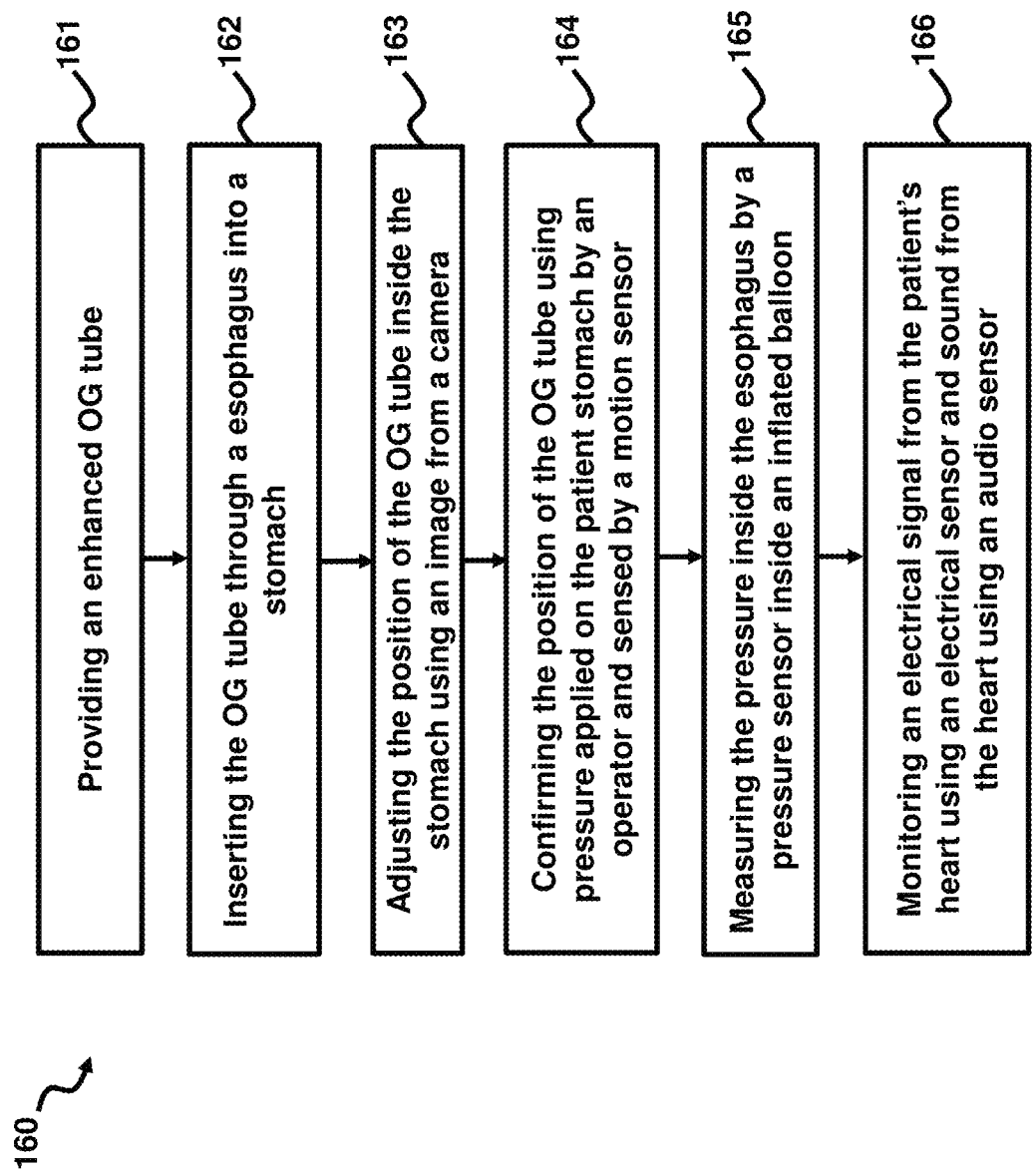
FIG. 16 is a flowchart illustrating a method for proper placement of an enhanced OG tube according to an embodiment herein.

FIG. 16, with reference to FIGS. 1 through 15B, illustrates a flow diagram according to the embodiments herein. As shown in FIG. 16, a method 160 of identifying the placement and use of the enhanced OG tube 120 inside a human body (e.g., esophagus 109 and stomach 107) is provided according to an embodiment herein. The method 160 comprises providing (161) an enhanced OG tube 120; inserting (162) the OG tube 120 through a esophagus 109 into a stomach 107; adjusting (163) the position of the OG tube 120 inside the stomach 107 using an image from the camera 126; confirming (164) the position of the OG tube 120 using pressure applied on the patient's stomach 107 by an operator and sensed by a motion sensor 127; measuring (165) the pressure inside the esophagus 109 by a pressure sensor 129 inside an inflated balloon 124; and monitoring (166) an electrical signal from the patient's heart using an electrical sensor 122 and sound from the heart using an audio sensor 123.

Figure 17:
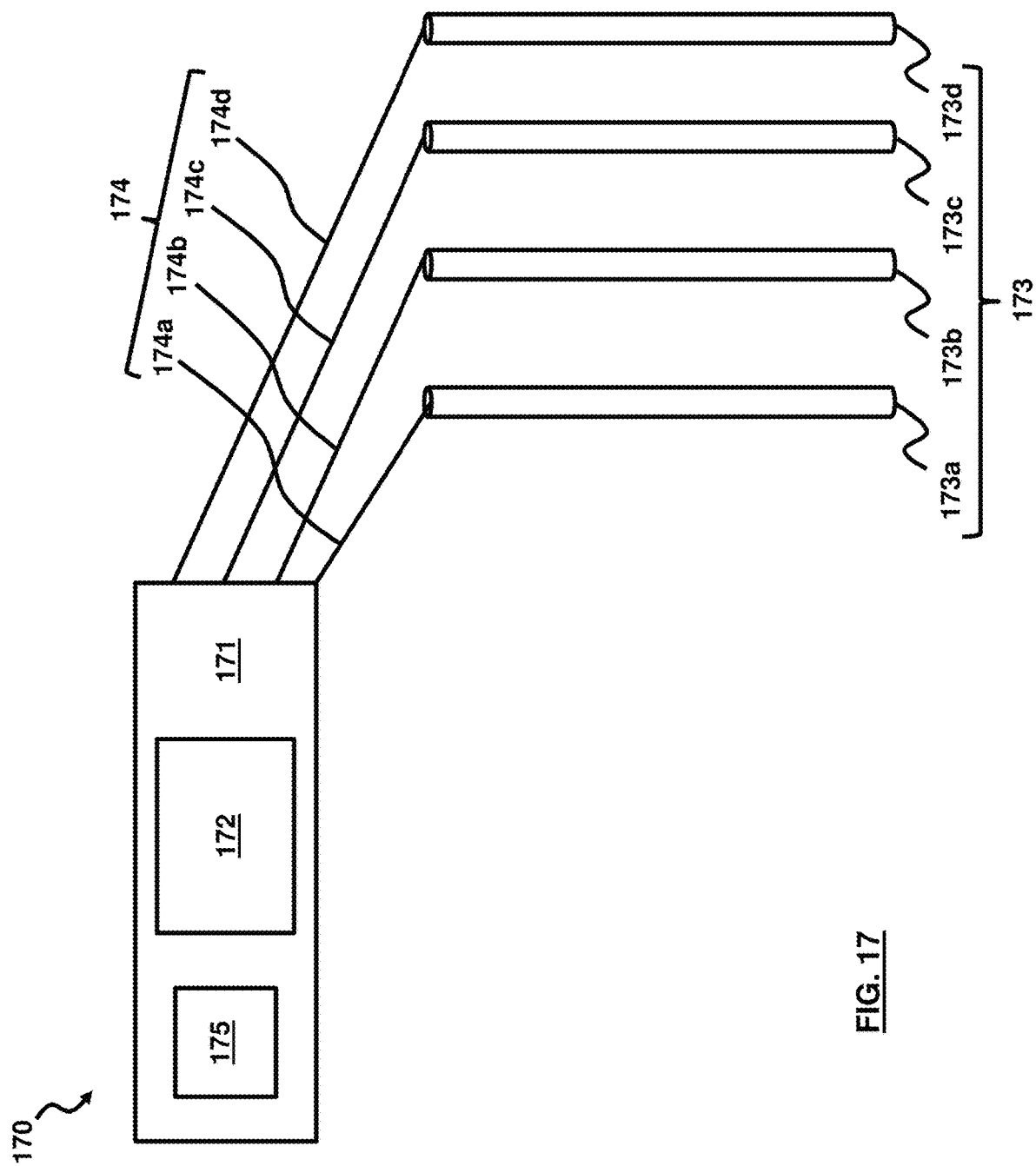
FIG. 17 illustrates a system including medical probes according to an embodiment herein.

FIG. 17, with reference to FIGS. 1 through 16, is a schematic diagram illustrating a system 170, according to an embodiment herein. System 170 comprises probes 173a, 173b, 173c, and 173d (collectively referred to herein as probes 173), connected to a device 171 via connections 174a, 174b, 174c, and 174d (collectively referred to herein as probes 174). System 170 may include any number of probes 173. Probes 173 may be any of the devices, longitudinal members, tubes, or inserts illustrated in FIGS. 1 through 16. For example, the probes 173 may include any of the longitudinal member 12 and camera 40 (with or without the semi-rigid cord 17 or the semi-rigid hollow cylinder 23), the longitudinal member 81 and the side camera 83, and the enhanced OG tube 120, with their various functionalities described herein.

Probes 173 communicate with the device 171 via connections 174, which may be wired or wireless connections. The connections 174 may be shared on a common channel, or each may be a specific channel or physical connection.

The device 171 includes a display 172 to display various inputs from the probes 173. For example, the display 172 may display any of the images from the camera 40, the side camera 83, or the camera 126, readings of the pressure sensor 129, readings form the motion sensor 127, and heart electrocardiogram (EKG) using readings from the electrical signal 122. The device 172 may include speaker 175 to play an audio signal detected by the audio sensor 123, according to an embodiment herein.

The embodiments herein allow the intubator's vision to extend beyond the vocal cords of a patient in an immediate confirmation of a proper placement of the ET tube. This is performed by replacing the conventional semi-rigid aluminum "stylet" that goes in the ET tube during insertion with a semi-rigid scope that will continue to provide the ET tube with the desired stiffness and shape in addition to immediate visualization of where the ET tube tip is. In an example, this scope has a length/depth marker at 35 cm from its tip. While inside the ET tube, the scope tip will be advanced to be placed next to the tip of the ET tube. The scope camera will display a picture in an attached screen. The picture will reflect the exact location of the ET tube tip. After advancing the ET tube through the vocal cords, the intubator will have an "immediate" visual impression of where the tip is by seeing "or not seeing" the very characteristic cartilage rings the trachea. This will alleviate esophageal intubation. Then, while in the trachea, both the ET tube and the scope will be advanced until the trachea ends. The visual landmark of the tracheal end is where it divides. Then, the 30-cm mark in the ET tube will be brought next to the 35-cm mark in the scope. This will bring the ET tube tip to be 5 cm above the end of the 10-cm trachea. This process can immediately avoid incorrect ET tube placement and will also abolish having to perform unnecessary confirmatory X-ray imaging.

Another aspect of the embodiments herein provides the ability to continue to utilize the current enormous supply of (PVC) NG/OG tubes without switching to a new line of very expensive OG/NG tubes equipped with cameras at their tips. The current (PVC) tubes have a standard design of a blunt tip and 6-8 small side openings to deliver the nutrition formulas to the patient's stomach. There is also a larger single 6 mm opening that allows suctioning the stomach content if clinically indicated. In an example, the embodiments herein provide a thin flexible endoscope of 2.5 mm diameter with a 5 mm "side" camera. The scope will be lubricated and introduced into the lumen of the standard PVC NG/OG tubes before placement. With the help of a thin layer of medical wax, the 5 mm side camera will fit into the 6 mm suction opening of the PVC-OG/NG tube. The side camera will display a picture of the tube's surroundings into an attached screen. Absence of visualizing cartilage rings will rule out incorrect tracheal placement and visualizing the characteristic folds of the stomach inner wall will confirm a proper placement. After that, the thin scope is pulled out of the NG/OG tube. Again, this will immediately avoid serious incorrect placement complications and abolishing an unnecessary confirmatory X-ray image.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A patient monitoring, feeding, and mechanical breathing system, said system comprising:
    an endotracheal (ET) probe comprising:
        an ET tube comprising a hollow cylindrical body;
        a first longitudinal member connected to a first camera; and
        a semi-rigid longitudinal member operatively connected to said first longitudinal member, wherein said first longitudinal member and said semi-rigid longitudinal member are configured to be inserted in said ET tube such that said first camera is aligned with a tip of said ET tube;
    an oral gastro (OG) probe comprising:
        an OG tube comprising:
            a hollow passage;
            a window on a sidewall of said hollow passage; and
            a plurality of feeding holes on said hollow passage;
        a second longitudinal member configured to be inserted in said hollow passage, said second longitudinal member comprising a side camera, configured to be placed facing said window on said sidewall of said hollow passage and held in place by a medical wax, wherein said side camera comprises a tapered side located on a proximal side of said side camera configured to reduce friction caused by the medical wax while removing said second longitudinal member and said side camera from said hollow passage;
    an enhanced OG probe, comprising:
        an enhanced OG tube longitudinal body;
        a second camera placed at a tip of said enhanced OG tube longitudinal body; and
        a motion sensor placed at said tip of said enhanced OG tube longitudinal body;
    a device communicatively coupled to said endotracheal probe, said OG probe, and said enhanced OG probe, wherein said device comprises a screen configured to display images from any of said first camera, said side camera, and said second camera.

2. The system of claim 1, wherein said semi-rigid longitudinal member comprises a semi-rigid cord operationally connected to said first camera and in parallel to said first longitudinal member.

3. The system of claim 1, wherein said semi-rigid longitudinal member comprises a semi-rigid hollow cylinder operationally connected to said first camera and configured to cover said first longitudinal member.

4. The system of claim 1, wherein said tapered side of said side camera is configured to assist removing said second longitudinal member from said OG tube by pulling said second longitudinal member out of said OG tube.

5. The system of claim 1, wherein said first camera, said side camera, and said second camera are configured to respectively assist proper placement of said ET tube, said OG tube, and said enhanced OG tube in a patient by providing image from inside said patient.

6. The system of claim 5, wherein said motion sensor of said enhanced OG tube is configured to provide conformation of said proper placement of said enhanced OG tube in said patient by sensing a pressure applied on said patient.

7. The system of claim 1, wherein said enhanced OG tube further comprises an electric sensor configured to:

detect an electric signal generated by a heart of said patient when said enhanced OG tube is in said patient; and generate an electrocardiogram signal to said device for generating an electrocardiogram graph of said heart of said patient on said screen.

8. The system of claim 1, wherein said enhanced OG tube further comprises an audio sensor configured to:

detect an audio signal generated by said patient's heart when said enhanced OG tube is in said patient; and convert said audio signal to a second electrical signal and transmit said second electrical signal to said device.

9. The system of claim 8, wherein said device further comprises a speaker, and wherein said speaker regenerates a second audio signal resembling said heart audio signal using said second electrical signal.

10. The system of claim 1, wherein said enhanced OG tube further comprises a balloon configured to inflate in an esophagus of a patient when said enhanced OG tube is in said patient.

11. The system of claim 1, wherein said enhanced OG tube further comprises a pressure sensor inside a balloon, and wherein said pressure sensor is configured to:

measure a pressure inside said esophagus of said patient when said balloon is inflated; and communicate said measurement of said pressure to said device to be displayed on said screen.

12. The system of claim 11, wherein said enhanced OG tube further comprises an elongated body comprising:

a first longitudinal hole configured to hold a first connector to said second camera;

a second longitudinal hole configured to hold a second connector to said motion sensor;

a third longitudinal hole configured to hold a third connector to a pressure sensor;

a fourth longitudinal hole configured to hold a fourth connector to an electrical sensor;

a fifth longitudinal hole configured to hold a fifth connector to an audio sensor; and a sixth longitudinal hole configured to create an airway to said balloon.

13. A patient monitoring, feeding, and mechanical breathing system, said system comprising:

an endotracheal (ET) probe comprising:

an ET tube comprising a hollow cylindrical body;

a first longitudinal member connected to a first camera; and a semi-rigid longitudinal member operatively connected to said first longitudinal member, wherein said first longitudinal member and said semi-rigid longitudinal member are configured to be inserted in said ET tube such that said first camera is aligned with a tip of said ET tube;

an oral gastro (OG) probe comprising:

an OG tube comprising:

a hollow passage;

a window on a sidewall of said hollow passage; and a plurality of feeding holes on said hollow passage;

a second longitudinal member configured to be inserted in said hollow passage, said second longitudinal member comprising a side camera, configured to be placed facing said window on said sidewall of said hollow passage and held in place by a medical wax, wherein said side camera comprises a tapered side located on a proximal side of said side camera configured to reduce friction caused by the medical wax while removing said second longitudinal member and said side camera from said hollow passage;

an enhanced OG probe, comprising:

an enhanced OG tube longitudinal body;

a second camera placed at a tip of said enhanced OG tube longitudinal body;

a motion sensor placed at said tip of said enhanced OG tube longitudinal body;

an electric sensor configured to:

detect an electric signal generated by a heart of said patient when said enhanced OG tube is in said patient; and generate an electrocardiogram signal to said device for generating an electrocardiogram graph of said heart of said patient on said screen;

an audio sensor configured to:

detect an audio signal generated by said patient's heart when said enhanced OG tube is in said patient; and convert said audio signal to a second electrical signal and transmit said second electrical signal to said device;

a balloon configured to inflate in an esophagus of a patient when said enhanced OG tube is in said patient;

a speaker that regenerates a second audio signal resembling said heart audio signal using said second electrical signal; and a device communicatively coupled to said endotracheal probe, said OG probe, and said enhanced OG probe, wherein said device comprises a screen configured to display images from any of said first camera, said side camera, and said second camera.

14. The system of claim 13, wherein said semi-rigid longitudinal member comprises a semi-rigid hollow cylinder operationally connected to said first camera and configured to cover said first longitudinal member.

15. The system of claim 13, wherein said first camera, said side camera, and said second camera are configured to respectively assist proper placement of said ET tube, said OG tube, and said enhanced OG tube in a patient by providing image from inside said patient.

16. The system of claim 15, wherein said motion sensor of said enhanced OG tube is configured to provide conformation of said proper placement of said enhanced OG tube in said patient by sensing a pressure applied on said patient.

17. The system of claim 13, wherein said enhanced OG tube further comprises a pressure sensor inside a balloon, and wherein said pressure sensor is configured to:

measure a pressure inside said esophagus of said patient when said balloon is inflated; and communicate said measurement of said pressure to said device to be displayed on said screen.

18. The system of claim 17, wherein said enhanced OG tube further comprises an elongated body comprising:

a first longitudinal hole configured to hold a first connector to said second camera;

a second longitudinal hole configured to hold a second connector to said motion sensor;

a third longitudinal hole configured to hold a third connector to a pressure sensor;

a fourth longitudinal hole configured to hold a fourth connector to an electrical sensor;

a fifth longitudinal hole configured to hold a fifth connector to an audio sensor; and a sixth longitudinal hole configured to create an airway to said balloon.

\* \* \* \* \*